(12) United States Patent
Haveri et al.

(10) Patent No.: US 8,586,930 B2
(45) Date of Patent: Nov. 19, 2013

(54) SIMPLIFIED BEAM SPLITTER FOR IR GAS SENSOR

(75) Inventors: Heikki Haveri, Humhari (FI); Kurt Peter Weckstrom, Frasavagen (FI)

(73) Assignee: General Electric Company, Schenectady, NY (US)

( * ) Notice: Subject to any disclaimer, the term of this patent is extended or adjusted under 35 U.S.C. 154(b) by 732 days.

(21) Appl. No.: 12/565,099

(22) Filed: Sep. 23, 2009

(65) Prior Publication Data

US 2010/0078563 A1    Apr. 1, 2010

(30) Foreign Application Priority Data

Sep. 30, 2008   (EP) ..................................... 08165473

(51) Int. Cl.
*G01J 5/02*   (2006.01)
(52) U.S. Cl.
USPC .......................................................... 250/343
(58) Field of Classification Search
USPC .......................................................... 250/343
See application file for complete search history.

(56) References Cited

U.S. PATENT DOCUMENTS

| | | | |
|---|---|---|---|
| 4,243,882 A | | 1/1981 | Yasujima et al. |
| 4,332,770 A | * | 6/1982 | Ishida et al. ..................... 422/78 |
| 5,070,245 A | * | 12/1991 | Rantala et al. ................. 250/343 |
| 5,464,982 A | | 11/1995 | Drucker et al. |
| 5,616,923 A | * | 4/1997 | Rich et al. ...................... 250/343 |
| 5,866,349 A | | 2/1999 | Lilja et al. |
| 5,900,635 A | * | 5/1999 | Weckstrom ..................... 250/345 |
| 6,509,567 B2 | * | 1/2003 | Boudet et al. .................. 250/345 |
| 6,512,230 B1 | | 1/2003 | von Lerber |
| 7,092,587 B1 | | 8/2006 | Denis |
| 2004/0000643 A1 | | 1/2004 | Karlsson |
| 2007/0241280 A1 | * | 10/2007 | Dainobu et al. ................ 250/343 |
| 2008/0011952 A1 | * | 1/2008 | Fabinski et al. ................ 250/344 |

FOREIGN PATENT DOCUMENTS

| | | |
|---|---|---|
| GB | 896686 | 5/1962 |
| JP | 8184558 A | 7/1996 |
| JP | 9033432 A | 2/1997 |

* cited by examiner

*Primary Examiner* — David Porta
*Assistant Examiner* — Midny Vu
(74) *Attorney, Agent, or Firm* — Global Patent Operation; Marc A. Vivenzio

(57) ABSTRACT

A non-dispersive single beam detection assembly in an infrared gas analyzer. The detection assembly comprises radiation source(s) providing infrared radiation, a measuring chamber, and a physical beam splitter for dividing said radiation beam into a reflected beam portion and a transmitted beam portion, or for combining a reflected beam portion and a transmitted beam portion into said radiation beam. A measuring detector receives one beam portions, and a reference detector receives another beam portion. Alternatively a measuring/reference detector receives both beam portions. Said transmitted beam portion has a first spectral intensity peak at shorter wavelengths with a first peak wavelength, and said reflected beam portion has a second spectral intensity peak at longer wavelengths with a second peak wavelength. There is a wavelength gap between said second peak wavelength and said first peak wavelength, which gap corresponds a wavelength shift of an optical interference filter with said second peak wavelength as tilted from its perpendicular position to an angled position. Said wavelength gap is at maximum 10% of the second peak wavelength, and at minimum 0.5% of the second peak wavelength.

13 Claims, 2 Drawing Sheets

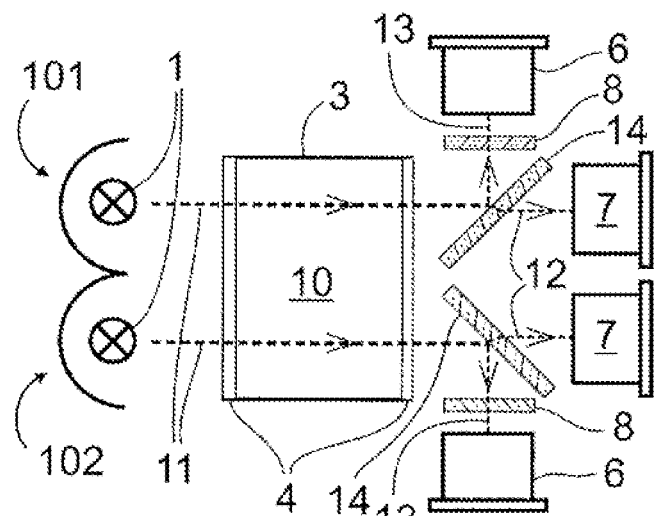
Fig. 4
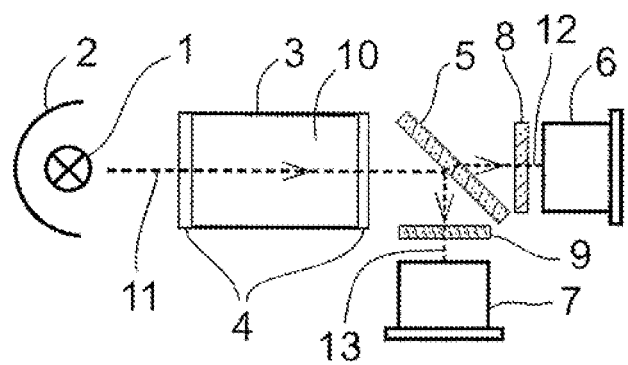
Fig. 5 *Prior Art*

SIMPLIFIED BEAM SPLITTER FOR IR GAS SENSOR

CROSS-REFERENCE TO RELATED APPLICATIONS

This application claims priority under 35 U.S.C. §119(a)-(d) or (f) to prior-filed, co-pending European patent application number EP08165473.3, filed on Sep. 30, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The subject matter disclosed herein relates generally to a gas measuring device based on infrared absorption and, specifically, to a simplified filter and beam splitter arrangement used to divide a source radiation into a measuring and a reference part or to combine the radiation from a measuring and a reference source into one radiation path. The measuring device is typically a single path non-dispersive infrared analyzer using narrow-band transmission filters to enable selectivity for a specific gas and a non-absorbing reference band. The device may have either one source and two detectors or two sources and one detector.

2. Description of Related Art

Beam splitters are used in optics for the purpose of dividing one beam into two parts or combining two beams into a single beam. Wavelength region or distribution and intensity ratio between the two separate beam portions depend upon the specific properties of the beam splitter. The most typical beam splitter is a thin plate of glass or plastic with one surface coated to be a semi-reflective mirror. One portion of the beam is transmitted through the beam splitter and the other portion is reflected, typically by 90 degrees if the angle of incidence is 45 degrees. Possible absorption in the beam splitter materials is here ignored and is usually very low for the designed wavelength regions. Further, a thin semi-reflective membrane, a pellicle, is a possible beam splitter solution but it may not be robust enough in many cases and it can be sensitive to temperature fluctuations, and its reliable fastening is also a problem. The coating is in most cases virtually independent of wavelength but it may also divide the spectral region into an upper and a lower part. Such a beam splitter is called dichroic and has the advantage that both the transmitted and the reflected radiation suffer little loss. However, the measuring and reference wavelength regions must be well separated for this kind of beam splitter to work with satisfaction. In such known beam splitters the dichroic beam splitter is made of a material which preferably deflects rays having a radiation wavelength in the range of 4.3 microns and alternately transmits wavelengths in the range of 3.7 microns.

It is known an apparatus for analyzing the breathing gases of a person for alcohol, the analysis being carried out on the basis of infrared radiation absorption properties. For this purpose the apparatus comprises a radiation source for providing an infrared radiation beam, a measuring chamber for selectively receiving the breathing gages of a person or ambient air, whereupon the radiation from the radiation source passes through the contents of the measuring chamber, a first detector for receiving radiation that has passed through the measuring chamber, and a first optical interference bandpass filter interposed in front of the detector along a path of the radiation beam. The first filter has a radiation wavelength transmission band for transmitting radiation of the transmission band wavelength through the filter to the first detector, while the reflected radiation has wavelengths outside the radiation wavelength transmission band. The first filter is here movable to a plurality of positions inclined with respect to the radiation beam for altering the radiation wavelength transmission band of the first filter. There is also a second detector positioned to receive radiation reflected from the surface of the first filter when it is moved to a given one of the plurality of positions. Means coupled to the first detector analyze the breathing gases for alcohol on the basis of radiation received by the first detector when it is in a plurality of positions. Comparison means coupled to the first and second detectors establish a relationship between the transmitted radiation received by the first detector and the reflected radiation received by the second detector when ambient air is in the measuring chamber for determining the suitability of ambient air as a reference gas mixture.

It is known a non-dispersive infrared measuring arrangement, in which the beam splitter may consist of two segments positioned on top of each other in a direction transversal to the beam direction of the radiation, which beam splitter segments are designed and manufactured to have different beam splitting ratios. For the second independent single path analyzer channel, the characteristics of the first beam splitter segment, i.e. the splitting ratio and the cross-over wavelength, are selected so that neither an additional measurement filter nor an additional reference filter is needed, but the beam splitter acts simultaneously as the actual beam splitter and as the measurement filter and as the reference filter. This is possible when the beam splitter has the bandpass characteristics corresponding to the absorption peak of the measured gas component, and the gas component does not have any other substantial absorption peak in the wavelength range, where the detector has sensitivity and/or the chamber windows have transmittance and/or the radiation source has emission. The other first independent single path analyzer channel is provided with an optical measurement filter, having a narrow passband, but no additional reference filter, but an additional analyzing filter in front of the measuring detector partial channel. This kind of arrangement is said to be useful when the beam splitter segment has a relatively narrow wavelength range, which is reflected to have a proper wavelength range for the reference partial channel, whereupon the transmitted wavelength range is in many cases too wide necessitating the measurement filter. Accordingly, both independent single path analyzer channels have measuring detectors positioned to receive the transmitting portion of the radiation beam and reference detectors positioned to receive the reflected portions of the radiation beam, while in the first analyzer channel there is a reference filter between the beam splitter and the reference detector in the reflected beam portion, which case means quite expensive construction, and in the second analyzer channel there is no reference filter in the reflected beam portion at all, in which case the reference detector system receives radiation from very wide wavelength range often causing problems or errors. The publication also discloses the electronic processing units for the two single path analyzer channels, whereupon the measurement partial channel and the corresponding reference partial channel of both analyzer channels is connected to one of the electronic processing units to provide the measurement signals and the reference signals thereto.

The beam splitters described above are called physical beam splitters because the complete beam aperture is available in both the transmitted and the reflected part as opposed to the so called geometrical beam splitters, where the radiation is mechanically divided into transmitting and reflecting parts. The beam splitters in this invention are physical beam splitters. In many cases the detectors must measure over a very narrow spectral wavelength range to be really selective for a specific gas. Using beam splitters as described above still necessitates in most cases an additional narrow bandpass filter, which is different from the beam splitter, in front of the measuring detectors. Then it is normally needed at least three optical components, one for the beam splitter and two further narrow-band filters, one for measuring partial channel and another for the reference partial channel, all three with different specifications, i.e. different wavelength ranges for transmittance and reflectance. Three separately designed filters with small wavelength tolerances are required to avoid e.g. an uncontrolled cross-talk. Dielectric filters for the infrared region are expensive so a simplified solution would be beneficial. Dielectric filters are, as generally known, interference filters, which are multilayer filters, the layers made of nonconductive material like some oxides, some fluorides, some sulfides, etc. the materials having at least two different refractive indices and arranged to have proper very small thicknesses in specified order, but not metallic layers, whereupon wanted edge, lowpass, highpass, bandpass, notch etc. properties are attained. Of course the wanted wavelength range shall be taken account when selecting materials and designing the construction.

A conventional single path infrared (IR) gas analyzer construction intended for measurements of a single gas using a reference sensor and a measuring is shown in FIG. 5. In this kind of detection assembly according to the prior there is an infrared source 1 with optional collimating or focusing optics 2 which directs the radiation as a radiation beam 11 into a measuring chamber 3 with input and output windows 4. Inside the measuring chamber is the gas 10 to be measured. If the chamber 3 is in a mainstream measuring adapter the gas flow would be perpendicular to the figure plane, otherwise the chamber could have input and output connections for the gas. The gas inputs and outputs are not shown in the figure. After the measuring chamber 3 the radiation enters a beam splitter 5 where the radiation is divided into a transmitted part 12 and a reflected part 13. The beam splitter is often a semi-reflective surface with minor wavelength dependence. Any wavelength would then split into a two roughly identical parts, a transmitted and a reflected one. An example of this is a partly metalized surface or a plate made of silicon or germanium or any other material, with high refractive index. Obviously, this arrangement wastes signal. If the measurement wavelength and the reference wavelength are clearly in separate regions a preferable beam splitter construction would be an interference filter transmitting an upper part of the spectrum and reflecting a lower part of it, or vice versa. Such an arrangement is called dichroic and has the advantage that both transmitted and reflected wavelengths are effectively transferred.

Another advantage is that the interference filter has very little absorption in wavelength regions intended for use. The transmitted radiation part 12, which is normally the measuring radiation, is transferred to a measuring detector 6 via a narrow-band filter 8. This filter makes the analyzer selective to a specific gas. e.g. carbon dioxide, which case the transmission band must coincide with the absorption peak of carbon dioxide. The reflected part of the radiation 13 is directed through a filter 9 to a reference detector 7, which serves as a non-absorbing reference to the measuring part. The filter 9 is normally of narrow-band type and the center wavelength is chosen so that the gas to be measured has minimal influence on the signal collected from the reference detector 7. A position close to the measuring wavelength is often advantageous since disturbing phenomena like water absorption and scattering, absorption from other gases; or thermal behavior of the filters are then as similar as possible. However it is very difficult to design two filters with transmission bands very close to each other without demanding requirements for wavelength tolerance. This affects the expenses of the construction. Therefore, this latter design is seldom used and instead the former design, in which the measuring and reference wavelength regions are clearly separated, is normally used.

BRIEF SUMMARY OF THE INVENTION

Gas analyzers like the ones described can be used for monitoring respiratory gases from a patient. In most cases at least carbon dioxide is measured. Therefore it is important to be able to produce such sensors cost effectively. This is especially true for mainstream sensors, which measure the respiratory gas directly at the ventilator tube. These sensors must also be small and light, especially those made for small children and neonates. Of course, also the gas sampling sidestream configuration benefits from the same features. At the same time the gas analyzer shall give measurement results that are reliable and accurate enough, which results shall not be affected too much by various disturbing agents and the like possibly present in the measuring chamber.

For these aims the non-dispersive single beam detection assembly has features as defined in claim 1, and the gas analyzer has features as defined in claim 9.

BRIEF DESCRIPTION OF THE SEVERAL VIEWS OF THE DRAWINGS

One or more embodiments of the invention are now described in detail with reference made to the accompanying drawings:

FIG. 4 illustrates a possible embodiment of an infrared gas analyzer, in which the non-dispersive single beam detection assemblies according to FIG. 1 are used.

FIG. 5 illustrates a gas measuring configuration according to prior art.

DETAILED DESCRIPTION OF THE INVENTION

Figure 2:
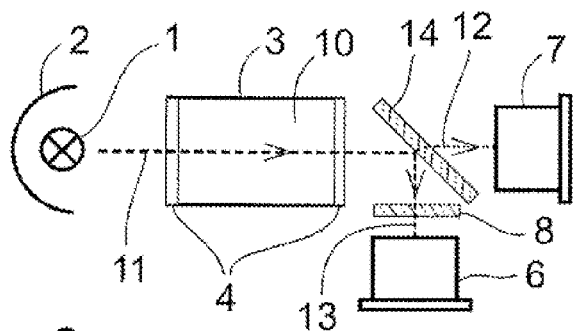
FIG. 2 illustrates an embodiment of a preferred non-dispersive single beam detection assembly using a narrow-band beam splitter and a similar narrow-band filter.
Figure 3:
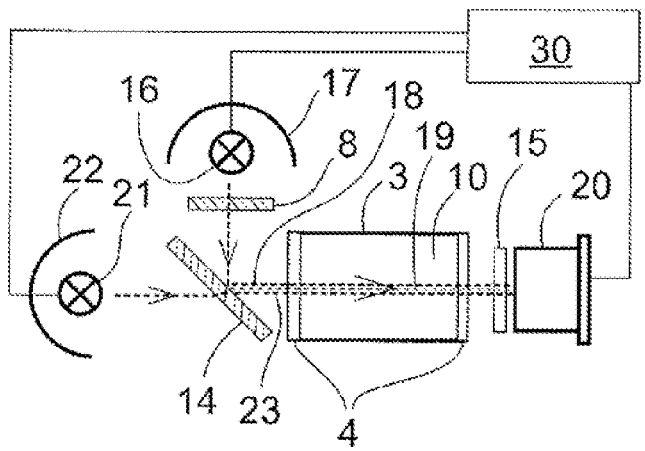
FIG. 3 illustrates another embodiment of a non-dispersive single beam detection assembly using a narrow-band beam splitter and a similar narrow-band filter.

One of the preferred embodiments of the invention is a non-dispersive single beam detection assembly in an infrared gas analyzer comprising, depending on the type of construction, at least one radiation source 1 or 16, 21, which provide(s) infrared radiation as a beam 11, 19 into and through a measuring chamber 3. The measuring chamber contains the gas mixture 10 with a gas component to be measured, whereupon the concentration of the gas component to be measured may be from zero to some maximum value. The assembly also comprises a physical beam splitter 14 either for dividing the radiation beam 11 into a reflected beam portion 13 and a transmitted beam portion 12, or for combining a reflected beam portion 18 and a transmitted beam portion 23 into the radiation beam 19. In the former alternative, i.e. with dividing beam splitter as shown in FIG. 2, the assembly has one radiation source 1, and the latter alternative, i.e. with combining beam splitter as shown in FIG. 3, the assembly has two radiation sources 16 and 21. There is a measuring detector 6 positioned to receive one of the beam portions, and a reference detector 7 positioned to receive another of the beam portion, or a measuring/reference detector 20 positioned to receive both the beam portions.

Figure 1:
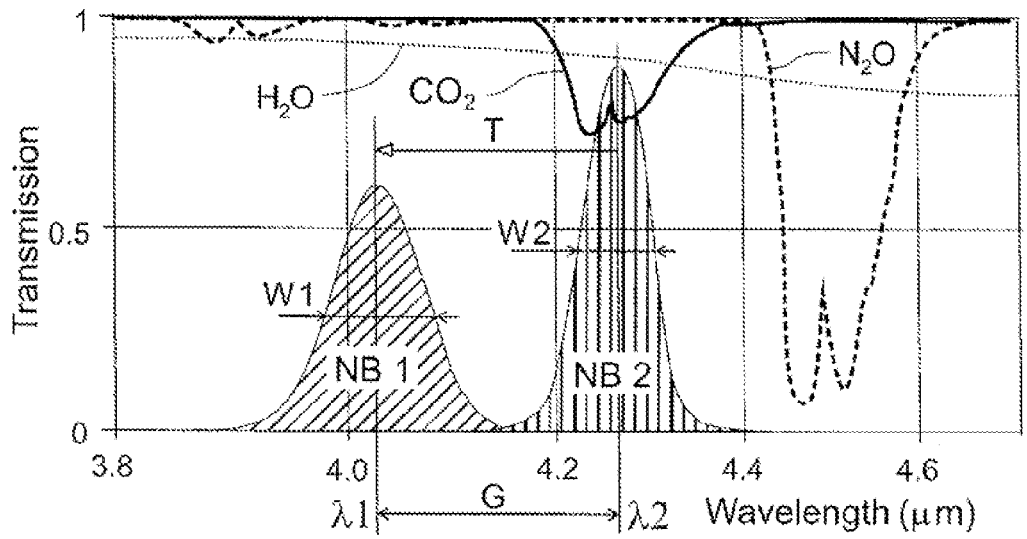
FIG. 1 illustrates a spectral region showing the absorption of carbon dioxide $CO_2$, nitrous oxide $N_2O$, and water $H_2O$ and the transmission band of a narrow-band filter NB measured at normal to a beam direction and 45 degrees incidence.

According to the invention in general the transmitted beam portion 12 or 23 has a first spectral intensity peak NB1 at shorter wavelengths with a first peak wavelength $\lambda 1$ and with a first half-bandwidth W1, as shown in FIG. 1. This transmitted beam portion 12, 23 hits directly after the beam splitter 14, i.e. without any further narrow-band interference filter, into to the reference detector 7, or into the measuring/reference detector 20. The reflected beam portion 13 or 18 has a second spectral intensity peak NB2 at longer wavelengths with a second peak wavelength $\lambda 2$ and a second half-bandwidth W2, as also shown in FIG. 1, but these wavelength and half-bandwidth properties are present in the beam portion only after the combination of the beam splitter 14 and the pass-band filter 8 that is the analyzing filter 8. Then this reflected and by analyzing filter filtered beam portion 13, 18 ends directly into to the measuring detector 6, or into the measuring/reference detector 20. Of course there is the measuring chamber 3 either before the beam splitter 14 and the analyzing filter 8 as in FIG. 2, or after the beam splitter 14 and the analyzing filter 8 as in FIG. 3. On one hand: In the embodiment of FIG. 2 the radiation is at first reflected by the beam splitter 14 and then filtered by optical pass-band filter 8 to have the second intensity peak NB2, and in the embodiment of FIG. 3 the radiation is at first filtered by optical pass-band filter 8 to have the second intensity peak NB2 and then reflected by the beam splitter 14. In both cases just that beam portion, which have the second peak wavelength $\lambda 2$ and a second half-bandwidth W2, is reflected sooner or later, and is accordingly the reflected beam portion 13, 18. On the other hand: In the embodiment of FIG. 2 the radiation is only transmitted through the beam splitter 14 to have the first intensity peak NB2, and in the embodiment of FIG. 3 the radiation is only transmitted through the beam splitter 14, too. This means that in both cases just that beam portion, which have the first peak wavelength $\lambda 1$ and a first half-bandwidth W1, is transmitted sooner or later, and is accordingly the transmitted beam portion 12, 23. About the beam splitter 14, which is a tilted passband filter, which initially has the second peak wavelength $\lambda 2$ with the second half-bandwidth W2, now having the shifted pass-band with the first peak wavelength $\lambda 1$ and the first half-bandwidth W1 then provides transmission of the radiation over this reference band—$\lambda 1$, W1, while outside this range the beam splitter 14 acts as a mirror, which means that this filter, which initially—in this document "initially" refers to values that are measured when an optical filter is perpendicular to the radiation direction, whereupon the incidence angle is 0° has the second peak wavelength $\lambda 2$ with a second half-bandwidth W2, when working as the beam splitter 14 now reflects radiation with the second peak wavelength $\lambda 2$ and a second half-bandwidth W2, i.e. the measuring band—$\lambda 2$, W2.

The first peak wavelength $\lambda 1$ is shorter than the second peak wavelength $\lambda 2$, and the second peak wavelength $\lambda 2$ is longer than the first peak wavelength $\lambda 1$, as obvious from the disclosure above. There is a wavelength gap G between the second peak wavelength $\lambda 2$ and the first peak wavelength $\lambda 1$, and this wavelength gap G corresponds a wavelength shift T of an optical interference filter, which initially has the second peak wavelength $\lambda 2$, as tilted from its perpendicular position to its angled position between 30° and 60° in respect to radiation direction. This mentioned optical interference filter or filters, which causes or cause the properties of the transmitted and reflected beam portions, has initially a second peak wavelength $\lambda 2$ and initial a second half-bandwidth W2 when the optical features of this optical interference filter are measured using radiation that comes and exits the optical filter in direction perpendicular to the plane of the filter, whereupon the normal of the filter plane is parallel to the radiation beam—when using the most established terminology. When just the mentioned or identical or similar optical interference filter is set in a tilted position, in which the normal of the filter plane has an angle between 30° and 60° in respect to radiation direction, or respectively the plane of the optical interference filter has an angle between 60° and 30° in respect to the radiation direction, the initial second peak wavelength $\lambda 2$ makes a shift T so as to be the first peak wavelength $\lambda 1$ and the bandwidth slightly changes so as to be the first half-bandwidth W1. The arithmetic sum of the first half-bandwidth W1 and the second half-bandwidth W2 (=W1+W2) is smaller than two times the wavelength gap G. In the case of FIG. 1 half-bandwidth W1≈W2≈0.1 μm and the gap G≈0.2 μm, whereupon W1+W2≈G, while 2×G would be 0.4 μm. The sum of the first half-bandwidth W1 and the second half-bandwidth W2 is preferably smaller than 1.5 times the wavelength gap, or may be smaller than the wavelength gap G. The sum can also be in some cases smaller than the wavelength gap G. Starting from the mentioned incidence angles from 30° to 60° the minimum of the gap G would be about 0.5% to 1% of the mean peak wavelength, like the second peak wavelength $\lambda 2$. Then there would be considerable overlapping between the first and the second spectral intensity peaks NB1 and NB2, but the peak wavelengths $\lambda 1$, $\lambda 2$ are of course different enabling analyzing of the gas component using a reference signal. The maximum of the gap G would be about 10% of the mean peak wavelength, like the second peak wavelength $\lambda 2$. It shall be noted that the value of the wavelength gap G and the value of the second half-bandwidth W2 are depending on the construction of interference/dielectric filter 8, 14, and as such, independent from each other. Of course, if we have a final piece of filter having a specific interference layer construction in hands, then the second half-bandwidth W2 is determined and also the wavelength gap G is determined when the incidence angle is specified for this filter unit. Typically the wavelengths within the first half-bandwidth W1 and wavelengths within the second half-bandwidth W2 are not substantially overlapping each other. Some overlapping can be allowable depending on the gas component to be measured and the gas analyzer construction. Half-bandwidth means, according to the established terminology, the width of a passband at half-power or half-intensity or half of peak transmittance points, specified typically in wavelength units. Accordingly, the wavelength gap G should be at maximum 10% of the second peak wavelength $\lambda 2$, and the wavelength gap G should be at minimum 0.5% of the second peak wavelength $\lambda 2$, but values between can also apply, like at maximum 6% of the second peak wavelength, and at minimum 1% of the second peak wavelength. The second peak wavelength $\lambda 2$ and the second half-bandwidth W2 of course match with an absorption peak of the gas component to be measured.

In the embodiment of FIG. 2 the detection assembly is implemented without the single measuring/reference detector 20, but instead the detection assembly has the measuring detector 6—for detecting the gas component signal—positioned to receive the reflected beam portion 13, and the reference detector 7—for detecting the reference signal—positioned to receive the transmitted beam portion 12. There is also a pair of dielectric optical filters 8, 14 having similar radiation transmission properties. This means that the mentioned two optical filters 8, 14 have practically the same transmission band, which has the second peak wavelength $\lambda 2$ and the second half-bandwidth W2, when measured perpendicular to the plane of the filters. These two filters can be made e.g. by preparing at first one larger filter, and then by cutting this larger filter into at least two separate pieces with smaller sizes, which separate pieces of filter now are similar or have initially the same second peak wavelength $\lambda 2$ and the same second half-bandwidth W2, but of course the different first peak wavelength $\lambda 1$ and the different first half-bandwidth W1 when tilted. One of these dielectric optical filters—i.e. one piece of filter—is positioned to be the physical beam splitter 14 dividing the infrared radiation beam 11 transmitted through the measuring chamber 3, into a part of the reflected beam portion 13 and into the transmitted beam portion 12. The other of these dielectric optical filters—i.e. another piece of filter—is positioned to be the analyzing filter 8 and so between the physical beam splitter 14 and the measuring detector 6, whereupon the reflected beam portion 13 is attained. This way the reference detector 7 receives the shifted reference band $\lambda 1$, W1 directly through the beam splitter 14 as the transmitted beam portion 12, and the measuring detector 6 receives the accurate, initial and non-shifted measuring band $\lambda 2$, W2 via the beam splitter 14 and through the initially similar optical bandpass filter 8 as the reflected beam portion 13. Of course there is one wide-band radiation source 1 providing infrared radiation source as a single beam 11 through the measuring chamber 3.

In the embodiment of FIG. 3 the detection assembly is implemented without the separate measuring detector 6 and the reference detector 7, but instead the detection assembly has the single measuring/reference detector 20—for detecting both the gas component signal and the reference signal—positioned to receive the transmitted beam portion 23 and the reflected beam portion IS incorporated in the radiation beam 19 that transmits through the measuring chamber 3. Here too, there is a pair of dielectric optical filters 8, 14 having similar radiation transmission properties. This means that the mentioned two optical filters 8, 14 have practically the same transmission band, which has the second peak wavelength $\lambda 2$ and the second half-bandwidth W2, when measured perpendicular to the plane of the filters. These two filters can be made as described in the previous chapter. One of these dielectric optical filters—i.e. one piece of filter—is positioned to be the physical beam splitter 14 making by combining the radiation beam 19 that is then transmitted through the measuring chamber 3, from the reflected beam portion 18 that is reflected just by this mentioned beam splitter and from the transmitted beam portion 23. The other of these dielectric optical filters—i.e. another piece of filter—is positioned to be the analyzing filter 8 and so between the physical beam splitter 14 and the radiation source 16, whereupon a part of the beam portion to be reflected as the disclosed reflected beam portion 18 is attained. This way the measuring/reference detector 20 receives both the shifted reference band $\lambda 1$, W1 directly through the beam splitter 14 as the transmitted beam portion 23, and the accurate, initial and non-shifted measuring band $\lambda 1$, W2 through the analyzing filter 8 and the initially similar beam splitter 14 as the reflected beam portion 18. There can be two wide-band radiation sources 16, 21, as shown in FIG. 3, or one wide-band radiation source, which wide-band radiation source(s) provide(s) infrared radiation for the reflected beam portion 18 and the transmitted beam portion 23 directly through the beam splitter or via the analyzing filter and the beam splitter, whereupon the radiation beam 19 is attained. If only one radiation source is used its radiation shall be divided into to parts, one for the transmitted beam portion 23 and the other for the reflected beam portion 18. In this embodiment there is also a chopper unit 30 that is connected to the one or two wide-band radiation source(s) 16, 21 and to the one measuring/reference detector 20, whereupon the reflected beam portion 18 and the transmitted beam portion 23 would be swapped, so that the transmitted beam portion 23 with the reference band $\lambda 1$, W1 and the reflected beam portion 18 with the measuring band $\lambda 2$, W2 are by turns sent through the measuring chamber and read in turn by the single measuring/reference detector 20. The chopper unit 30 can work electronically or mechanically, and is not described in detail, because choppers are familiar to persons skilled in the art. Though this alternative of FIG. 3 is slightly more complicated than the embodiment of FIG. 2, the advantage of this arrangement is that the detector drift is identical to both measuring and reference signals. Of course, it is required that the sources are stable enough. A cheap broadband filter 15 in front of detector can be used to block ambient radiation if needed.

It is as such well known that a dielectric narrow-band filter shifts its transmission band towards shorter wavelengths if the angle of incidence of radiation deviates from normal=perpendicular to plane of the filter. An example of this is shown in FIG. 1. Infrared absorption curves for carbon dioxide $CO_2$, nitrous oxide $N_2O$, and liquid water $H_2O$ are shown in a spectral region from 3.8 to 4.7 μm together with the transmission characteristics of a typical narrow-band filter measured at incidence angle 0°, i.e. in case when the radiation hits the filter at direction perpendicular to the filter plane, and at incidence angle 45°, i.e. when the radiation hits the filter at direction 45° in respect to the filter plane. Such a filter is used at incidence normal to the filter plane in order to measure carbon dioxide in conventional NDIR analyzers. The amount of wavelength shift T with angle of incidence depends on the filter construction but is normally such that the transmission band has been relocated outside the original transmission band when at 45° angle of incidence. The transmission maximum and band hall-bandwidth may change slightly with angle of incidence as indicated in the spectrum in FIG. 1. Mostly these changes are of minor importance. As can be seen from the spectrum, no absorption from carbon dioxide falls within the shifted band or the first intensity peak NB1 with the first peak wavelength $\lambda 1$ and the first half-bandwidth W1 at incidence angle 45° as compared to the perpendicular situation being the second intensity peak NB2 with the second peak wavelength $\lambda 2$ and the second half-bandwidth W2 at incidence angle 0°. This filter property can be utilized in gas measuring devices, as gas analyzers, in such a way that the signal measured through the inclined filter serves as a reference signal, which is hence measured by the reference detector 7 using the shifted first peak wavelength $\lambda 1$ and the first half-bandwidth W1, while the actual gas signal is measured by the measuring detector 6 using the second peak wavelength $\lambda 2$ and the second half-bandwidth W2 at incidence normal to the filter. With the narrow-band transmission filter or narrow bandpass filter is here understood an interference filter designed to have a transmission band with a half-bandwidth smaller than 2% of the peak wavelength $\lambda 2$ or a typical half-bandwidth at maximum 2% of the second peak wavelength $\lambda 2$. Depending on the design and need the half-bandwidth of the transmission band can be as low as 0.5% or up to about 10%.

It shall be noted that the reference detector 7 shall receive radiation which is substantially independent from the variable concentration of the gas component to be measured and, if only possible, independent from all other gas components, whose concentration may change during the measuring procedure, but clearly dependant on all other things that can change during the measuring procedure. Accordingly, the reference detector continuously gives data about disturbing issues, so that the reading from the measuring detector can be corrected. I.e. the measuring detector should have only such data that is caused by the gas components to be measured only, but because it may receive some error causing data too, the reference detector shall give details with which the errors in the measuring detector can be corrected during measuring procedure. Using a reference has nothing to do with the calibration of the device, which is made prior to measuring procedure! For reference purpose the separate reference detector or the single detector during reference period of the swapping is provided with an optical reference filter, which has a transmission wavelength range, within which the gas component to be measured does not have a substantial absorption. But in order to the have the intended error correction the route of beam into the reference detector should be as long as possible the same as the route of beam into the measuring detector. The reference detector shall operate simultaneously with the measuring detector or practically simultaneously, i.e. with so small time difference that it can be neglected in the use in question.

Another disturbing factor is nitrous oxide, which may be used during anesthetics, and which influences the measured value of carbon dioxide not only by minor overlapping spectral regions but also through collision broadening. Even if the gas does not have noticeable absorption at the same wavelength region as carbon dioxide it will influence the absorption in such a way that increased concentration of nitrous oxide will increase the absorption of carbon dioxide. The reason for this is collision broadening, a molecular interaction between the two different molecules. The individual rotational absorption lines of carbon dioxide will broaden as a result of the interaction. This decreases the transmission and, consequently, decreases the signal, which is the sum of transmissions integrated over the wavelength band of the narrow-band filter. Such collision broadening is normally compensated for by measuring nitrous oxide separately, but in this case a certain amount of compensation is introduced automatically, because nitrous oxide has a minor absorption at the reference wavelength band but not at the carbon dioxide measurement region, as shown in FIG. 1. Of course, the amount of compensation depends on the amount of absorption at the reference region and the location of the reference region depends on the angle of incidence and the inherent angular dependence of the filter construction. However, the compensated signal is better than the uncompensated signal in most cases, or the error caused by the collision broadening can be made small enough so that it does not inflict notable errors. In order to adjust the compensation the angle of incidence could be altered from the typical 45° or the filter construction could be changed or the filter could be designed to transmit at the proper wavelength at 45° incidence. In this latter case, however, the analyzing filter 8 cannot be identical with the narrow-band beam splitter so the advantages of using identical filters would be lost.

Another advantage of locating the reference band $\lambda 1$, W1 close to the measuring band $\lambda 2$, W2 is influence from liquid water, both as absorption and as scattering from condensed water on the windows of the measuring chamber. Compensation for disturbing absorption of water is also essential in a mainstream respiratory sensor. Water easily condenses on the windows of the measuring chamber unless they are heated. Antifogging treatment can be used but then a thin water film resides on the window surfaces. The water absorption curve is shown in the spectrum in FIG. 1. It is not constant with wavelength at the carbon dioxide absorption region but the resulting error is small enough for the reference signal to handle. The absorption at the location of the reference is in this case not exactly the same as that at the measuring band but the compensation resulting from a ratio calculation is often good enough. The liquid water easily condensates on the windows of the measuring chamber if the measured gas is very humid like breathing gas. This could happen in a mainstream measuring configuration as described above. The water normally forms droplets on the window and creates scattering. Scattering is wavelength dependent in such a way that short wavelengths are scattered more than long wavelengths. Since scattering reduces the measurable radiation from the infrared source in the analyzer the influence would be greater at the shorter reference wavelength than at the measuring wavelength. This fact would compensate for the absorption differences and water would not have noticeable influence on the carbon dioxide reading under normal conditions.

There are also many other advantages related to this simplified construction. The measurement and reference wavelength regions are close to each other in a controlled way with no need for demanding tolerances. The thermal behavior is also similar if the same filter material is used for beam splitter 14 and filter 8. Because of the reduced number of needed parts a smaller and lighter analyzer construction is possible. This is very essential e.g. when designing a mainstream respiratory sensor for neonatal use.

In the described cases carbon dioxide was used as the preferred gas since it is present and generally measured in respiratory gas. This invention is not restricted to the measurement of carbon dioxide but any single gas with infrared absorption could be involved.

The detectors 6 and 7 and 20 can be any type of infrared sensitive devices but typically they are thermopiles or they can be constructed of pyroelectric or semiconductor material if fast response time is needed. The signals are further processed in amplifiers and other proper electronics according to well-known technique. This is not shown in the figure but is obvious to anyone acquainted with gas sensors, the radiation sources 1, 16, 21 can be any type of wide-band sources, e.g. any type of thermal radiation source like miniature lamps or silicon based radiators, or light emitting diodes (LED) or the like, which emit infrared radiation over a radiation band having a large enough half-bandwidth. In the embodiment of FIG. 2 the single wide-band source 1 has a half-bandwidth larger than the wavelength gap G between the second peak wavelength $\lambda 2$ and the first peak wavelength $\lambda 1$. In the embodiment of FIG. 2 the wide-band sources 16, 21 has a half-bandwidths larger than the first half-bandwidth W1, or larger than the second half-bandwidth W2. Typically the half-bandwidths are at least $\frac{1}{20}$—e.g. 200 nm—of the second peak wavelength $\lambda 2$, or at least one fifth—e.g. 800 nm—of the second peak wavelength $\lambda 2$. In many cases the radiation band has a half-bandwidth that is much wider, may be thousands of nanometers.

The described non-dispersive single beam detection assembly, which initially work for analyzing one gas component only, can be modified in fact multiplied to form an infrared gas analyzer, with which several gas components can be analyzed. For this purpose the infrared gas analyzer has one measuring chamber 3 for gas mixture 10 with gas components to be measured, and at least two non-dispersive single beam detection assemblies 101, 102. The infrared radiation of the detection assemblies 101, 102 pass as one or two beam(s) 11 or 19 through the one measuring chamber 3. In the first non-dispersive single beam detection assembly 101 its second peak wavelength $\lambda 2$ and second half-bandwidth W2 match with an absorption peak of a first gas component to be measured. In the second non-dispersive single beam detection assembly 102 the second peak wavelength $\lambda 2$ and second half-bandwidth W2 match with an absorption peak of a second gas component to be measured. It shall be noted that the measuring band $\lambda 2$, W2—could be marked as $\lambda 2_1$, W$2_1$—of the first detection assembly 101 deviates from the measuring band $\lambda 2$, W2—could be marked as $\lambda 2_2$, W$2_2$—of the second detection assembly 101. Of course the infrared gas analyzer may have more than two detection assemblies, each of which having a measuring band $\lambda 2$, W2 different from each other. This way a multitude of gas components, like $CO_2$, CO, NO, $N_2O$, alcohols etc., can be analyzed.

What is claimed is:

1. A non-dispersive single beam detection assembly in an infrared gas analyzer, the assembly comprising:
   one wide-band radiation source providing infrared radiation as a beam;
   a measuring chamber for a gas mixture with a gas component to be measured;
   a physical beam splitter for dividing said radiation beam transmitted through the measuring chamber into a reflected beam portion and a transmitted beam portion;
   a measuring detector positioned to receive the reflected beam portion, and a reference detector positioned to receive the transmitted beam portion; wherein the detection assembly comprises:
      a pair of dielectric optical pass-band filters having the same peak wavelength and the same half-bandwidth when perpendicular to the radiation direction, one of the dielectric optical filters positioned to be the physical beam splitter dividing the infrared radiation as a beam, and another of the dielectric optical filters positioned to be an analyzing filter between the physical beam splitter and the measurement detector, wherein said transmitted beam portion has a first spectral intensity peak at shorter wavelengths with a first peak wavelength and a first half-bandwidth, and said reflected beam portion after the analyzing filter has a second spectral intensity peak at longer wavelengths with a second peak wavelength and a second half-bandwidth; and
      there is a wavelength gap between said second peak wavelength and said first peak wavelength, which wavelength gap corresponds to one wide-band to a wavelength shift of an optical interference filter with said second peak wavelength as tilted from its perpendicular position to an angled position between 30° and 60° in respect to radiation direction; and
      said wavelength gap is at maximum 10% of the second peak wavelength, and at minimum 0.5% of the second peak wavelength.

2. A non-dispersive single beam detection assembly according to claim 1, wherein an arithmetic sum of the first half-bandwidth and the second half-bandwidth is smaller than two times the wavelength gap.

3. A non-dispersive single beam detection assembly according to claim 1, wherein said dielectric optical filters are narrow-band dielectric optical filters having a second half-bandwidth smaller than 5% of the second peak wavelength, or at maximum 3% of the second peak wavelength.

4. A non-dispersive single beam detection assembly according to claim 1, wherein said second peak wavelength and said second half-bandwidth match with an absorption peak of the gas component to be measured.

5. A non-dispersive single beam detection assembly according to claim 1, wherein said wide-band source has a half-bandwidth larger than the wavelength gap between said second peak wavelength and said first peak wavelength.

6. A non-dispersive single beam detection assembly according to claim 3, wherein said wide-band source has a half-bandwidth larger than the first half-bandwidth, or larger than the second half-bandwidth.

7. An infrared gas analyzer, comprising a non-dispersive single beam detection assembly according to claim 1, wherein said infrared gas analyzer has one measuring chamber for gas mixture, and at least two non-dispersive single beam detection assemblies wherein their infrared radiation pass as beam(s) to said one measuring chamber, whereupon:
   in a first non-dispersive single beam detection assembly said second peak wavelength and said second half-bandwidth match with an absorption peak of a first gas component to be measured; and
   in a second non-dispersive single beam detection assembly said second peak wavelength and said second half-bandwidth match with an absorption peak of a second gas component to be measured.

8. A non-dispersive single beam detection assembly in an infrared gas analyzer, the assembly comprising:
   one or two wide-band radiation sources providing infrared radiation as a beam;
   a measuring chamber for a gas mixture with a gas component to be measured;
   a physical beam splitter for combining a reflected beam portion and a transmitted beam portion into the radiation beam;
   a measuring/reference detector positioned to receive both the reflected beam portion, and the transmitted beam portion that is then transmitted through the measuring chamber;
   wherein the detection assembly comprises:
      a pair of dielectric optical pass-band filters having the same peak wavelength and the same half-bandwidth when perpendicular to the radiation direction, one of the dielectric optical filters positioned to be the physical beam splitter combining the infrared radiation to a beam, and another of the dielectric optical filters positioned to be an analyzing filter between the physical beam splitter and the radiation source for the reflected beam portion; and
      a chopper unit connected to the one or two wide-band radiation sources and to the measuring/reference detector swapping the reflected beam portion and the transmitted beam portion, wherein the transmitted beam portion has a first spectral intensity peak at shorter wavelengths with a first peak wavelength and a first half-bandwidth, and said reflected beam portion has a second spectral intensity peak at longer wavelengths with a second peak wavelength and a second half-bandwidth; and there is a wavelength gap between said second peak wavelength and said first peak wavelength, which wavelength gap corresponds to a wavelength shift of an optical interference filter with said second peak wavelength as tilted from its perpendicular position to an angled position between 30° and 60° in respect to a radiation direction; and said wavelength gap is at maximum 10% of the second peak wavelength, and at minimum 0.5% of the second peak wavelength.

9. A non-dispersive single beam detection assembly according to claim 8, wherein an arithmetic sum of the first half-bandwidth and the second half-bandwidth is smaller than two times the wavelength gap.

10. A non-dispersive single beam detection assembly according to claim 9, wherein said dielectric optical filters are narrow-band dielectric optical filters having a second half-bandwidth smaller than 5% of the second peak wavelength, or at maximum 3% of the second peak wavelength.

11. A non-dispersive single beam detection assembly according to claim 9, wherein said second peak wavelength and said second half-bandwidth match with an absorption peak of the gas component to be measured.

12. A non-dispersive single beam detection assembly according to claim 9, wherein said wide-band source has a half-bandwidth larger than the wavelength gap between said second peak wavelength and said first peak wavelength.

13. A non-dispersive single beam detection assembly according to claim 9, wherein said wide-band source has a half-bandwidth larger than the first half-bandwidth, or larger than the second half-bandwidth.

* * * * *

UNITED STATES PATENT AND TRADEMARK OFFICE
CERTIFICATE OF CORRECTION

PATENT NO. : 8,586,930 B2
APPLICATION NO. : 12/565099
DATED : November 19, 2013
INVENTOR(S) : Haveri et al.

It is certified that error appears in the above-identified patent and that said Letters Patent is hereby corrected as shown below:

In the Specification

In Column 2, Line 8, delete "gages" and insert -- gases --, therefor.

In Column 3, Line 60, delete "material," and insert -- material --, therefor.

In Column 4, Line 15, delete "gases;" and insert -- gases, --, therefor.

In Column 5, Lines 26-27, delete "into to the" and insert -- into the --, therefor.

In Column 5, Line 36, delete "into to the" and insert -- into the --, therefor.

In Column 7, Line 50, delete "portion IS" and insert -- portion 18 --, therefor.

In Column 8, Line 6, delete "λ1, W2" and insert -- λ2, W2 --, therefor.

In Column 8, Line 15, delete "into to" and insert -- into two --, therefor.

In Column 8, Line 52, delete "hall-bandwidth" and insert -- half-bandwidth --, therefor.

Signed and Sealed this
Fifteenth Day of April, 2014

Michelle K. Lee
*Deputy Director of the United States Patent and Trademark Office*